US007105637B2

(12) United States Patent
Shackleton et al.

(10) Patent No.: US 7,105,637 B2
(45) Date of Patent: Sep. 12, 2006

(54) DEHYDRO-ESTRIOL (8-DHE3) AND DEHYDRO-PREGNANETRIOL (7-DHPT), METHODS OF THEIR SYNTHESIS

(75) Inventors: Cedric Shackleton, Oakland, CA (US); Li-Wei Guo, Houston, TX (US); William K. Wilson, Houston, TX (US)

(73) Assignees: William Marsh Rice University, Houston, TX (US); Children's Hospital & Research Center at Oakland, Oakland, CA (US)

( * ) Notice: Subject to any disclaimer, the term of this patent is extended or adjusted under 35 U.S.C. 154(b) by 476 days.

(21) Appl. No.: 10/367,096

(22) Filed: Feb. 14, 2003
(Under 37 CFR 1.47)

(65) Prior Publication Data

US 2003/0220314 A1    Nov. 27, 2003

Related U.S. Application Data

(60) Provisional application No. 60/357,272, filed on Feb. 15, 2002.

(51) Int. Cl.
*A61K 38/00* (2006.01)
(52) U.S. Cl. .................................................. 530/350
(58) Field of Classification Search ................. 530/350
See application file for complete search history.

(56) References Cited

FOREIGN PATENT DOCUMENTS

WO       WO 01/92893       12/2001

OTHER PUBLICATIONS

Dehydro-oestriol and dehydropregnanetriol are candidate analytes for prenatal diagnosis of Smith-Lemli-Opitz syndrom. Prenat Diagn. Mar. 2001;21(3):207-12/ (In IDS of Jul. 2003).*
Midgestational maternal urine steroid markers of fetal Smith-Lemli-Opitz (SLO) syndrome (7-dehydrocholesterol 7-reductase deficiency). Steroids. Jul. 1999;64(7):446-52. (In IDS of Jul. 2003).*
Shackleton et al. Equine type estrogens produced by a pregnant woman carrying a Smith-Lemli-Opitz syndrome fetus J Clin Endocrinol Metab. Mar. 1999;84(3):1157-9 (In IDS of Jul. 2003).*
Shackleton et al. Midgestational maternal urine steroid markers of fetal Smith-Lemli-Opitz (SLO) syndrome (7-dehydrocholesterol 7-reductase deficiency). Steroids. Jul. 1999;64(7):446-52. (In IDS of Jul. 2003).*
Abuelo, et al., "Prenatal detection of the cholesterol biosynthetic defect in the Smith-Lemli-Opitz syndrome by the analysis of amniotic fluid sterols", *Am J Med Genet*, (1995) vol. 56: 281-285.
Andersson, et al., "Adrenal insufficiency In Smith-Lemli-Opitz Syndrome", *Am. J. Med Genet*, (1999) vol. 82 (5): 382-384.
Bradley, et al. "Levels of unconjugated estriol and other maternal serum markers in pregnancies with Smith-Lemli-Opitz (RSH) syndrome fetuses", *Am J Med Genet*, (1999) vol. 82:355-358.
Clayton. "Disorders of cholesterol biosynthesis", *Arch. Dis. Child*, (1998) vol. 78: 185-189.

Dallaire, et al. "Prenatal diagnosis of Smith-Lemli-Opitz syndrome is possible by measurement of 7-dehydrocholesterol in amniotic fluid", *Prenat. Diagn.*, (1995) vol. 15: 855-858.
Donnai, et al. "The lethal multiple congenital anomaly syndrome of polydactyly, sex reversal, renal hypoplasia, and unilobular lungs", *J. Med. Genet.* (1986) vol. 23: 64-71.
Fitzky, et al. "Mutations in the delta-7-sterol reductase gene in patients with the Smith-Lemli-Opitz syndrome", *Proc. Natl. Acad. Sci. USA*(1998) vol. 95: 8181-8186.
Glass, et al. "Steroid sulphatase deficiency is the major cause of extremely low oestriol production at mid-pregnancy: A urinary steroid assay for the discrimination of steroid sulphatase deficiency from other causes", *Prenat. Diagn.*, (1998) vol. 18: 789-800.
Li-Wei Guo, et al. "Synthesis of Ring B Unsaturated Estriols. Confirming the Structure of a Diagnostic Analyte for Smith -Lemil-Opitz Syndrome," (2001) Organic Letters, vol. 3, No. 16, pp. 2547-2550.
Irons, et al., "Defective cholesterol biosynthesis in Smith-Lemli-Opitz syndrome", *Lancet*, (1993) vol. 341:141.
Irons, et al. "Prenatal diagnosis of Smith-Lemli-Opitz syndrome", *Prenat. Diagn.*, (1998) vol. 18: 369-372.
Kelley. "Inborn errors of cholesterol biosynthesis", *Adv. Pediat.*, (2000) vol. 47: 1-53.
Kratz, et al. "Prenatal diagnosis of the RSH/Smith-Lemli-Opitaz syndrom", Am. J. Med. Genet. vol. 82: 376-381 (1999).
McGaughran, et al. "Prenatal diagnosis of Smith-Lemli-Opitz syndrome", *Am. J. Med. Genet.*, (1995) vol. 56: 269-271.
McKeever, et al. "Smith-Lemli-Opitz syndrome II: A disorder of the fetal adrenals?", *J. Med. Genet.*, (1990) vol. 27: 465-466.
Mills, et al. "First trimester prenatal diagnosis of Smith-Lemli-Opitz syndrome (7-dehydrochloesterol) reductase deficiency", *Pediatr. Res.*, (1996) vol. 39: 816-819.
Moebius, et al. "Molecular cloning and expression of the human delta 7-sterol reductase", *Proc. Natl. Acad. Sci. USA*, (1998) vol. 95: 1899-1902.
Palomaki, et al. "Maternal serum screening for Down syndrome in the United States: A 1995 survey", *Am. J. Med. Genet.*, (1997) vol. 176: 1046-1051.
Rossiter, et al. "Smith-Lemli-Opitz Syndrome: Prenatal diagnosis by quantification of cholesterol precursors in amniotic fluid", *American Journal of Medical Genetics*, (1995) vol. 56: 272-275.
Shackleton. "Mass spectrometry in the diagnosis of steroid-related disorders and in hypertension research", *J. Steriod Biochem. Molec. Biol.*, (1993) vol. 45: 127-140.

(Continued)

*Primary Examiner*—Bruce R. Campell
*Assistant Examiner*—Maury Audet
(74) *Attorney, Agent, or Firm*—Richard A. Schwartz; Carol L. Francis; Bozicevic, Field & Francis LLP

(57) ABSTRACT

The invention provides isolated dehydro-estriol (8-DHE$_3$) and dehydro-pregnanetriol (7-DHPT), and methods of their synthesis. These compounds are useful in diagnosis of Smith-Lemli-Optiz syndrome (SLOS).

15 Claims, 1 Drawing Sheet

OTHER PUBLICATIONS

Shackleton, et al. "Equine type estrogens produced by a pregnant woman carrying a Smith-Lemli-Opitz syndrome fetus", *J. Clin. Endrocrinol. Metab.*, (1999) vol. 84: 1157-1159.

Shackleton, et al. "Midgestational maternal urine steriod markers of fetal Smith-Lemli-Opitz syndrome (7-dehydrocholesterol 7-reductase deficiency)", *Steroids*, (1999) vol. 64 446-452.

Shackleton, et al. "Neonatal urinary steroids in Smith-Lemi-Opitz Syndrome associated with 7-dehydrocholesterol reductase deficiency", *Steroids*, (1999) vol. 64:481-490.

Shackleton, et al. "Dehydro-oestriol and dehydropregnanetroil are candidate analytes for prenatal diagnosis of Smith-Lemli-Opitz syndrome", *Prenat. Diagn.*, (2001) vol. 21: 207-212.

Sharp, et al. "First-trimester diagnosis of Smith-Lemli-Opitz syndrome", *Prenat. Diagn.*, (1997) vol. 17(4): 355-361.

Smith, et al. "A newly recognized syndrome of congenital nomalies", *J. Pediat.*, (1964) vol. 64: 210-221.

Steiner, et al. "Smith-Lemli-Opitz syndrome",*eMedicine J.*, (Apr. 4, 2001) vol. 2(4).

Steiner, et al. "Smith-Lemli-Opitz syndrome", *eMedicine J.*, (Feb. 5, 2002) vol. 3(2).

Tint, et al. "Defective cholesterol biosynthesis associated with the Smith-Lemli-Opitz syndrome", *N. Engl. J. Med.*, (1994) vol. 330: 107-113.

Tint, et al. "Fetal Smith-Lemli-Opitz syndrome can be detected accuratley and reliably by measuring amniotic fluid dehydrocholesterols", *Prenat. Diagn.*, (1998) vol. 18: 651-658.

Wassif et al., "Mutations in the human Sterol$\Delta^7$-Reductase Gene at 11q12-13 Cause Smith-Lemli-Opitz Syndrome,", Am. J. Hum. Genet. 63:55-62, 1998.

Waterham, et al. "Smith-Lemli-Opitz Syndrome is Cuased by Mutations in the 7-Dehydrocholesterol Reducatase Gene", *Am. J. Hum. Genet.*, (1998) vol. 63: 329-338.

\* cited by examiner

DEHYDRO-ESTRIOL (8-DHE3) AND DEHYDRO-PREGNANETRIOL (7-DHPT), METHODS OF THEIR SYNTHESIS

CROSS-REFERENCE TO RELATED APPLICATIONS

This application claims the benefit of U.S. provisional application Ser. No. 60/357,272, filed Feb. 15, 2002, which application is incorporated by reference herein in its entirety.

GOVERNMENT RIGHTS AND JOINT RESEARCH AGREEMENT

This invention was made with government support under federal grant nos. HL-49122 and RO3-HD39707 awarded by National Institute of Health. The United States Government may have certain rights in this invention. This invention was made pursuant to a joint research agreement between Children's Hospital and Research Center at Oakland and William Marsh Rice University.

FIELD OF THE INVENTION

The present invention relates to chemically synthesized compounds useful as analytes in the detection of Smith-Lemli-Optiz syndrome.

BACKGROUND OF THE INVENTION

Smith-Lemli-Optiz/RSH syndrome (SLOS) is a genetic disorder that affects the development of children both before and after birth. SLOS affects about 1:20,000 individuals. The syndrome was first described in 1964 in three boys with poor growth, developmental delay, and a common pattern of congenital malformations including cleft palate, genital malformations, and polydactyly (extra fingers and toes). In 1993 scientists discovered that children with SLOS are unable to make sufficient cholesterol.

The Smith-Lemli-Opitz syndrome (SLOS) is caused by impaired activity of the enzyme 3β-hydroxsterol, $\Delta^7$-reductase (7DHCR)(Irons et al., Lancet 341: 1414, 1993; Tint et al., N Engl J Med 330: 107–113, 1994), which is involved in the enzymatic conversion of 7-dehydrocholesterol to cholesterol, in one of two proposed routes of cholesterol biosynthesis (Scheme 1). The defect in 7DHCR results in an abnormal accumulation of 7- and 8-dehydrocholesterol (1 and 2). More than 60 enzyme mutations have been detected in SLOS-affected individuals (Fitzky et al., Proc Natl Acad Sci USA 95: 8181–8186, 1998; Moebius et al., Proc Natl Acad Sci USA 95: 1899–1902, 1998; Wassif et al., Am J Hum Genet 63: 329–338, 1998).

Scheme 1. Conversion of fetal $\Delta^{5,7}$ and $\Delta^{5,8}$ sterols to choloesterol

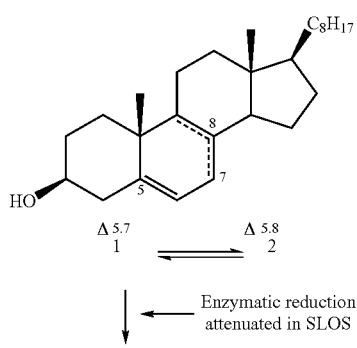

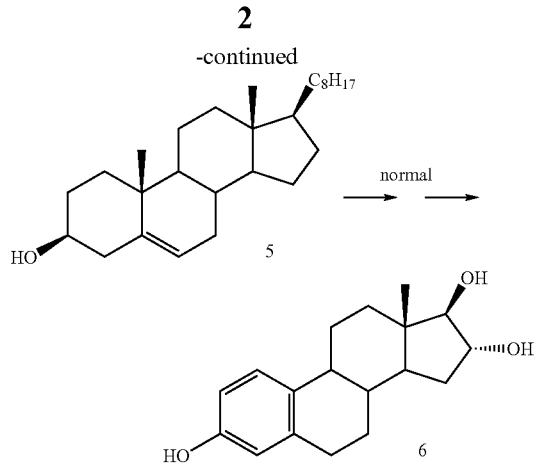

The challenge in prenatal diagnosis has been the identification of a non-invasive test that involves detection of definitive and SLOS-specific analyte(s), and which can be performed early in pregnancy. Many of the conventional SLOS screening assays involve detecting varying levels of 7-DHC, cholesterol or estriol ($E_3$) or a combination thereof, in chorionic villus (CV) or amniotic fluid samples, each of which are invasive tests and can pose a risk to the fetus. TABLE 1 lists the most common conventional SLOS markers for the screening of SLOS affected fetuses.

Table 1: Exemplary SLOS Markers
  Low Cholesterol levels in CV biopsies and amniotic fluid.
  Increased 7-DHC levels (Dehydrocholesterol) in CV and amniotic fluid.
  Increased 8-DHC levels (dehydrocholesterol II) in CV and amniotic fluid.
  Low unconjugated estriol levels in serum (non-specific marker)

Since fetal cholesterol is a precursor to estriol ($E_3$), $E_3$ is decreased in SLOS affected pregnancies (Donnai et al., J Med Genet 23: 64–71, 1986; McKeever and Young, J Med Genet 27: 465–466, 1990; Abuelo et al., Am J Med Genet 56: 281–285, 1995; Rossiter et al., Am J Med Genet 56: 272–275, 1995). However, detection of $E_3$ levels is not specific for SLOS-affected pregnancies. Currently, unconjugated serum estriol ($uE_3$) is measured in about 50% of all United States pregnancies as part of the "triple marker screening" for chromosomal aneuploidies and neural tube defects (Palomaki et al., Am J Med Genet 176: 1046–1051, 1997). In 1999, Bradley and co-workers (Bradley et al., Amer. J Med. Gen. 82:355–358, 1999) published a retrospective study of 26 SLOS pregnancies in which $uE_3$ in serum had been measured and determined that the mean $uE_3$ level was 0.23 of normal median (multiples of the median, MOM). Assaying for low estriol levels in maternal serum $MsuE_3$ along with sonography have also been suggested for diagnosing RSH/SLOS (Kratz, L. E., Kelley, R. I., Amer. J. Med. Gen. 82:376–381, 1999) as well as identifying patients with low maternal urinary levels of estriol (McKeever and Young, 1990) at mid-gestation.

Many SLOS diagnostic methods have been suggested in which the level of 7-DHC is detected due to the increase of this cholesterol precursor in SLOS affected patients. High levels of 7-DHC and 8-DHC have been detected in amniotic fluid and in CV biopsies of SLOS patients (Rossiter, J. P. et. al., Amer. J. Med. Gen. 56:272–275, 1995; Tint, G. S. et. al., Prenat. Diagn. 18:651–658, 1998; Irons, M. B., Tint, G. S., Prenat. Diagn. 18:369–372, 1998; Kratz, L. E., Kelley, R. I.,

*Amer. J. Med. Gen.* 82:376–381, 1999). High levels of 7-DHC have also been detected in CV biopsies of SLOS patients as early as the first trimester (Sharp, P. et al., *Prenat. Diagn.*, 17(4): 355–361, 1997). In addition to detection of 7-DHC and 8-DHC, high levels of lathosterol (cholest-7-en-3beta-ol), a 7-DHC precursor, have also been detected in amniotic fluid.

Mills, K. et. al., *Pediatric Research* 39(5): 816–819 (1996) describe a method for detecting SLOS by determining the ratio of 7-DHC (a cholesterol precursor) to cholesterol in chorionic villus (CV) samples. Mills et al. determined that cholesterol synthesis via 7-DHC occurs in the placenta and/or fetus at 10 weeks of gestation and that prenatal diagnosis by CV biopsy is possible. While this test can detect SLOS early in gestation, CV biopsy is an invasive procedure and is associated with some risk to the fetus and patient.

Recently, it was shown that mid-gestational urine from a SLOS affected pregnancy contains metabolites unsaturated analogs of the compounds estriol ($E_3$) and pregnanetriol (PT). These compounds were suggested to be synthesized or metabolized from fetal 7- or 8-DHC (Shackleton et al., *Steroids*. 1999a, 64(7): 446–52; Shackleton et al., *J. Clin. Endocrinol. Metab.* 1999b, 84(3): 1157–9; Shackleton et al., *Steroids*. 1999c, 64(7): 481–90).

Shackleton et al 1999a, disclose that either 7-DHPT or 8-DHPT of the 3,16,20 and 3,17,20 (triol structures) series was present in the maternal urine of one healthy 35 year-old women carrying a SLOS fetus at 17 weeks gestation. The authors provisionally characterize the SLOS metabolite as 5β-pregn-7(or 8-)-ene-3α,17α,20α-triol; 5β-pregn-7(or 8-)-ene-3α,16α,20α-triol; 5α-pregn-7(or 8-)-ene-3α,16α,20α-triol; 5α-pregn-7(or 8-)-ene-3α,17α,20α-triol and/or 5α-pregn-7(or 8-)-ene-3β,16α, 20α-triol. The authors indicated that the major SLOS metabolite compound is either 5β-pregn-7-ene-3α,17α,20α-triol (7-DHPT) and/or 5β-pregn-8-ene-3α,17α,20α-triol (8-DHPT). The authors did not indicate if the tentative SLOS metabolite was a mixture of the two epimers or pure 7-DHPT or 8-DHPT and no isolation of the specific compound was attempted. Furthermore, Shackleton et al. 1999a did not show detection of the analytes prior to 17 weeks gestation.

In a separate study of three young infants affected with SLOS, the authors detected a SLOS metabolite(s) and provisionally identified the compound(s) as 3β, 16α-dihydroxy-5,7-pregnadien-20-one; 3β, 16α-dihydroxy-5,8 (or 9-)pregnadien-20-one; homologues of 16α-hydroxy-DHEA, as well as the 7- or 8-epimer of 5β-pregnene-3α,17α,20α-triol (Shackleton et al., *Steroids*. 1999c, 64(7): 481–90). In short, while these studies narrow the possibilities of the identity of a unique SLOS analyte, they failed to confirm the identification due to the complexity of the mass spectra profile of the biological sample and the lack of appropriate reference compounds.

While these two SLOS specific metabolites were tentatively characterized by Shackleton et al., the actual structures and identification of the two SLOS specific analytes ($\Delta^7$ or $\Delta^8$) was not determined. Depending upon the sensitivity of the detection system, a detectable amount of these SLOS analyte may be found in normal patients, an assay which only detected the presence of a epimer mixture of these compounds or the wrong epimer without proper controls, could lead to a high frequency of false positives and false negatives, making the assay unpredictable, unreliable and not commercially viable. These risks of false positives and false negatives are further exacerbated when one considers that low levels of SLOS analyte levels are found in affected SLOS individuals, thus necessitating the use of sensitive detection methods such as gas chromatography/mass spectroscopy (GC/MS).

Currently, only pregnancies at 25% risk for SLOS are routinely subjected to testing by Dehydrocholesterol (DHC) measurement, with secondary screening of SLOS based on a finding of low $E_3$ now being considered. However, since there are multiple causes of low maternal $E_3$ levels, DHC measurement in amniotic fluid or villus tissue currently remains necessary for confirming diagnosis of SLOS. Unfortunately, these methods involve the analysis of compounds which are found in substantial quantities in both normal and SLOS affected patients, making the incidence of false positives higher than may be reasonably acceptable. False positives are particularly intolerable where a fetal diagnosis of SLOS may result in the mother's decision to abort. Also, these procedures are invasive in nature, making the diagnostic testing of DHC levels, in some cases, expensive, cumbersome, impractical, and even dangerous to the fetus and mother.

Thus, there is a need for compounds that can serve as standards for the analysis of SLOS analytes in the diagnosis of SLOS. The invention addresses this need.

SUMMARY OF THE INVENTION

The invention provides isolated dehydro-estriol (8-$DHE_3$) and dehydro-pregnanetriol (7-DHPT), and methods of their synthesis. These compounds are useful in diagnosis of Smith-Lemli-Optiz syndrome (SLOS).

Figure 1:
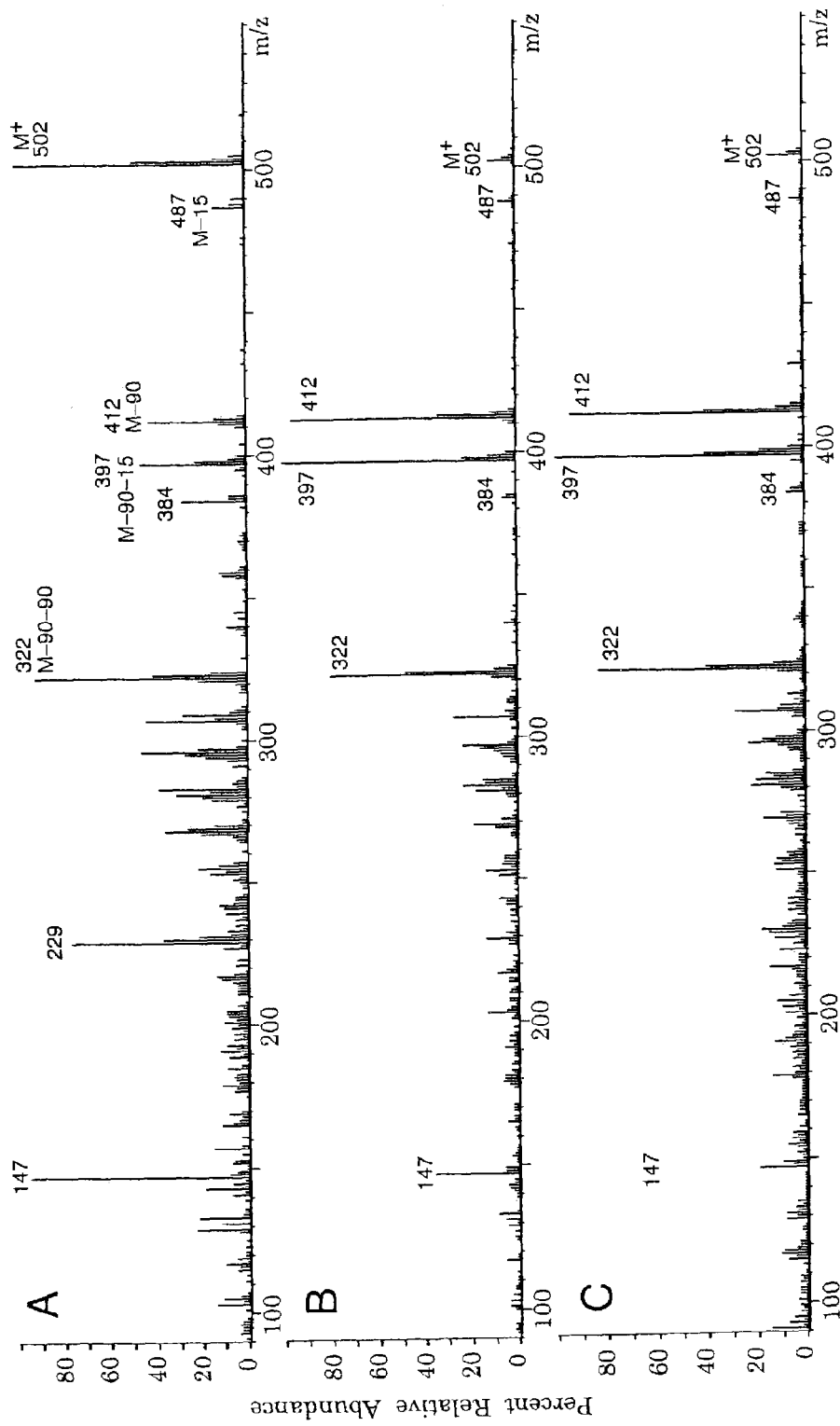
FIG. 1 is the gas chromatography/mass spectroscopy (GC/MS) spectra of tris-TMS derivatives of chemically synthesized 7-dehydroestriol (A), 8-dehydroestriol (B), and the dehydroestriol isolated from urine (C).

Before the present invention is described, it is to be understood that this invention is not limited to particular embodiments described, as such may, of course, vary. It is also to be understood that the terminology used herein is for the purpose of describing particular embodiments only, and is not intended to be limiting, since the scope of the present invention will be limited only by the appended claims.

Where a range of values is provided, it is understood that each intervening value, to the tenth of the unit of the lower limit unless the context clearly dictates otherwise, between the upper and lower limits of that range is also specifically disclosed. Each smaller range between any stated value or intervening value in a stated range and any other stated or intervening value in that stated range is encompassed within the invention. The upper and lower limits of these smaller ranges may independently be included or excluded in the range, and each range where either, neither or both limits are included in the smaller ranges is also encompassed within the invention, subject to any specifically excluded limit in the stated range. Where the stated range includes one or both of the limits, ranges excluding either or both of those included limits are also included in the invention.

Unless defined otherwise, all technical and scientific terms used herein have the same meaning as commonly understood by one of ordinary skill in the art to which this invention belongs. Although any methods and materials similar or equivalent to those described herein can be used in the practice or testing of the present invention, the preferred methods and materials are now described. All publications mentioned herein are incorporated herein by reference to disclose and describe the methods and/or materials in connection with which the publications are cited.

It must be noted that as used herein and in the appended claims, the singular forms "a", "and", and "the" include plural referents unless the context clearly dictates otherwise. Thus, for example, reference to "a derivative" includes a plurality of such derivatives and reference to "the compound" includes reference to one or more compounds and equivalents thereof known to those skilled in the art, and so forth.

The publications discussed herein are provided solely for their disclosure prior to the filing date of the present application. Nothing herein is to be construed as an admission that the present invention is not entitled to antedate such publication by virtue of prior invention. Further, the dates of publication provided may be different from the actual publication dates which may need to be independently confirmed.

DETAILED DESCRIPTION OF THE INVENTION

Overview

The invention generally involves two isolated compounds useful as analytes of SLOS: 1) 8-dehydro-estriol (8-DHE$_3$) and 2) 5β-pregn-7-ene-3α,17α,20α-triol (7-DHPT). By "SLOS analyte" is meant a compound which is indicative of risk of SLOS, and is generically used herein to refer to 8-DHE$_3$ and to 7DHPT. "Isolated" as used herein is meant that the compound is at least 60%, by weight, free from the naturally-occurring organic molecules with which it is naturally associated, including other epimers of the compound. Preferably, an isolated SLOS analyte preparation is at least 75%, more preferably at least 90%, and most preferably at least 99%, by weight, SLOS analyte. An isolated SLOS analyte may be obtained, for example, by extraction from a biological sample, or by chemical synthesis. Purity can be measured by any appropriate method, e.g., chromatography, HPLC analysis, GC/MS, and the like.

The invention also encompasses 8-DHE$_3$, 7-DHPT, derivatives of 8-DHE$_3$ and 7-DHPT (e.g., which are produced during the preparation and analysis of a biological sample being analyzed), and salts of 8-DHE$_3$ and of 7-DHPT. In one aspect of particular interest, the invention encompasses compositions consisting essentially of or consisting of 8-DHE$_3$; 7-DHPT; or a derivative or salt thereof. By "consisting essentially of" is meant that the composition includes the recited compound as well as other compounds or agents, with the proviso that any additional compounds or agents does not interfere with the characterization or analysis of the compound, e.g., by chromatography or mass spectroscopy, or both.

Salts of 8-DHE$_3$ and 7-DHPT encompassed by the invention can include, for example, addition salts of common physiologically compatible inorganic and organic acids. Salts of the compounds of the invention can be prepared using standard procedures known to those skilled in the art of synthetic organic chemistry and described, for example, by J. March, Advanced Organic Chemistry: Reactions, Mechanisms and Structure, 4th Ed. (New York: Wiley-Interscience, 1992). Acid addition salts are prepared from the free base (e.g., compounds having a neutral —NH$_2$ or cyclic amine group) using conventional means, involving reaction with a suitable acid. Typically, the base form of the compound is dissolved in a polar organic solvent such as methanol or ethanol and the acid is added at a temperature of about 0° C. to about 100° C., preferably at ambient temperature. The resulting salt either precipitates or may be brought out of solution by addition of a less polar solvent. Suitable acids for preparing acid addition salts include both organic acids, e.g., acetic acid, propionic acid, glycolic acid, pyruvic acid, oxalic acid, malic acid, malonic acid, succinic acid, maleic acid, fumaric acid, tartaric acid, citric acid, benzoic acid, cinnamic acid, mandelic acid, methanesulfonic acid, ethanesulfonic acid, p-toluenesulfonic acid, salicylic acid, and the like, as well as inorganic acids, e.g., hydrochloric acid, hydrobromic acid, sulfuric acid, nitric acid, phosphoric acid, and the like. An acid addition salt may be reconverted to the free base by treatment with a suitable base. Acid addition salts of particular interest include the citrate, fumarate, succinate, benzoate and malonate salts.

Preparation of basic salts of acid moieties which may be present (e.g., carboxylic acid groups) are prepared in a similar manner using a base such as sodium hydroxide, potassium hydroxide, ammonium hydroxide, calcium hydroxide, magnesium hydroxide, trimethylamine, or the like.

Compositions containing the compounds of the invention comprise an amount of the compound of the invention and an excipients or carrier, particularly an excipient or carrier suitable for use in chromatographic (e.g., gas, liquid, HPLC, and the like) and/or mass spectrometry analysis, and which are compatible with the compounds of the present invention, which carrier or excipients does not interfere with the characterization or analysis of the compound. Exemplary excipients or carriers include, but are not necessarily limited to, organic acids and their salts and esters, inorganic compounds such as inorganic calcium salts and oxides, higher alcohols, and other the like.

Derivatives of 8-DHE3 and of 7-DHPT are also contemplated by the invention. Of particular interest are derivatives of 8-DHE$_3$ and derivatives of 7-DHPT suitable for GC and/or GC/MS analysis (e.g., 8-DHE$_3$ and/or 7DHPT derivative produced by silyation, alkylation, acylation, and the like).

A more detailed description of each of these compounds, as well as their isolation and synthesis, is described below.

8-dehydro-estriol (8-DHE$_3$)

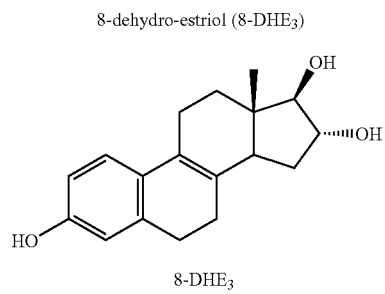

8-DHE$_3$

A Ring B unsaturated estriol has been identified by the inventors as a specific metabolite associated with SLOS which is useful in the diagnostic of Smith-Lemli-Opitz syndrome prenatally. 8-dehydro-estriol (8-DHE$_3$) is an abnormal metabolite produced in SLOS affected individuals from the high levels of dehydrocholesterols found in SLOS individuals due to the enzymatic reduction and attenuation which inhibits dehydrocholesterols to be converted to cholesterol (Scheme 2).

Scheme 2. Abnormal Metabolism of fetal $\Delta^{5,7}$ and $\Delta^{5,8}$ sterols to either $\Delta$ 7,8 dehydroestriols.

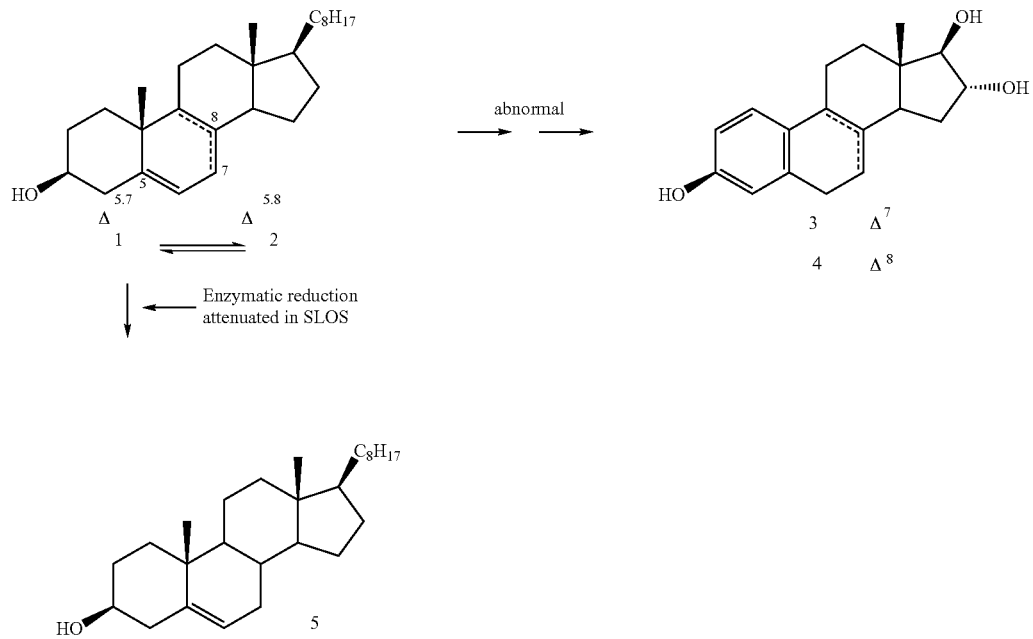

8-DHE$_3$ is thought to be a metabolite of the 8-dehydrocholesterol epimer which itself originates from 7-DHC through activity of an isomerase enzyme. The identification of the specific DHE$_3$ epimer associated with SLOS enables the development of SLOS diagnostic tests which are standardized and calibrated to a chemically synthesized and isolated 8-DHE$_3$ compound, further providing accuracy and reliability to the SLOS diagnostic analysis.

8-DHE$_3$ Chemical Synthesis

Considering the small amounts of material required for bioanalytical purposes, synthesis of 8-DHE$_3$ focused on partial synthesis from available estrogens, such as equilin, equilenin (10), and the Torgov diene. In a standard synthetic approach to estriols, the 16-hydroxyl is introduced by acid hydrolysis of a 16α, 17α-epoxide formed from the enol acetate of estrone. However, application of this method to equilin resulted in aromatization to 16α-hydroxyequilenin. Another known approach to 16-hydroxylation entails 16-bromination of estrone, followed by hydrolysis in DMF to the ketol. Although many unsaturated 17-ketosteroids can be selectively brominated at C-16 with CuBr$_2$ in refluxing methanol, this reaction was reported to give a complex mixture for equilin. Conditions for implemented the simple ring D manipulations shown in the retrosynthetic analysis (Scheme 3) without triggering the indicated side reactions, namely aromatization of ring B, epimerization at C-14, double-bond isomerization, and ketol rearrangement.

Scheme 3.

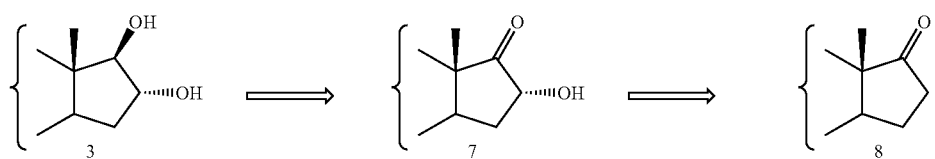

POTENTIAL SIDE REACIONS

| ISOMERIZATION, EPIMERIZATION | KETOL INTERCHANGE | AROMATIZATION |
|---|---|---|
| strongacid or base (from 3, 7, or 8) | base (from 7) | air, acid, base, or free radicals (from 3, 7, or 8) |

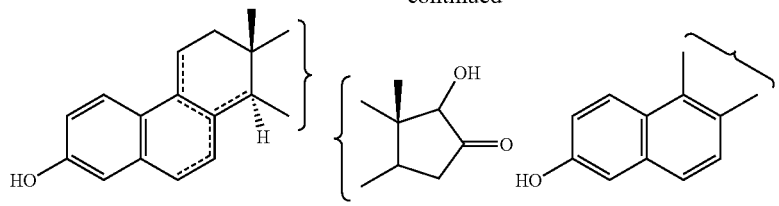

$\Delta^8$, $\Delta^{9(11)}$, $\Delta^6$, $\Delta^{8(14)}$,
and 14β epimers

The synthesis of 8-DHE$_3$ was completed by converting Equilin (8) in three steps to 7-dehydroestriol, which was isomerized to 8-dehydroestriol (Scheme 4). An exemplary scheme for the synthesis of 8-DHE$_3$ is described in the Examples below.

Scheme 4.

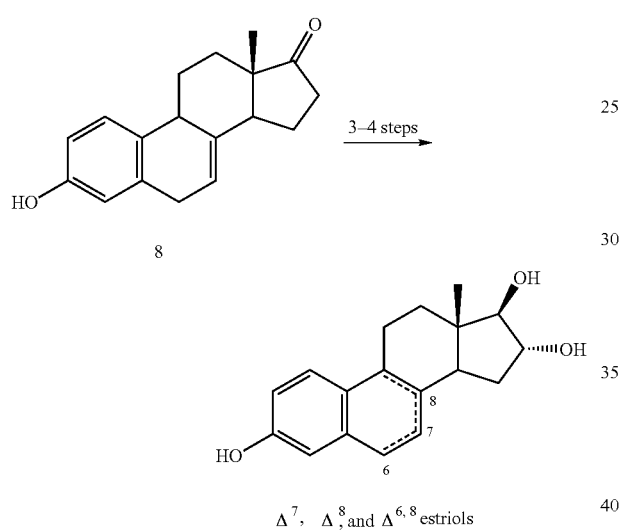

$\Delta^7$, $\Delta^8$, and $\Delta^{6,8}$ estriols

The compound 8-dehydroestriol (8-DHE$_3$) (14) may be prepared from various commercially available estrogens using a variety of known chemical synthetic techniques. One synthetic approach to 8-DHE$_3$ (14), shown in Scheme 3 and described in the following examples, utilized equilin (8). Briefly, equilin (8) was halogenated (specifically, brominated) to form a 16-haloequilin, as exemplified by the 16-bromoequilins (9a), (9b), which both hydrolyzed cleanly to give 16α-hydroxyequlilin (7). Reduction of 16α-hydroxyequlilin (7) (e.g., using Sodium borohydride) yielded 7-dehydroestriol (3). Treatment of 7-dehydroestriol (3) with Li/ethylene diamine provided 8-DHE$_3$ (14). Notably, direct treatment of 16α-hydroxyequlilin (7) did not provide the 8-dehydro compound (14).

5β-pregn-7-ene-3α, 17 α, 20 α-triol (7-DHPT)

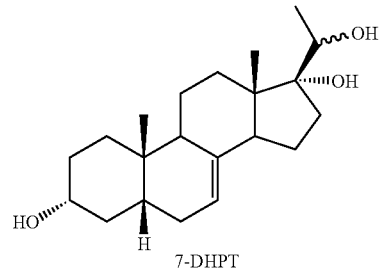

7-DHPT Chemical Synthesis

5β-Pregn-7-ene-3α,17α,20R-triol and its 20S isomer (6a and 6b) were prepared in five steps from the commercially available 17α-hydroxypregnenolone diacetate (1). The chemical synthesis is shown in Scheme 5.

Scheme 5. Chemical synthesis of 5β-Pregn-7-ene-3α, 17a, 20R-triol and its 20S isomer (6a and 6b) from 17α-hydroxypregnenolone diacetate (1).

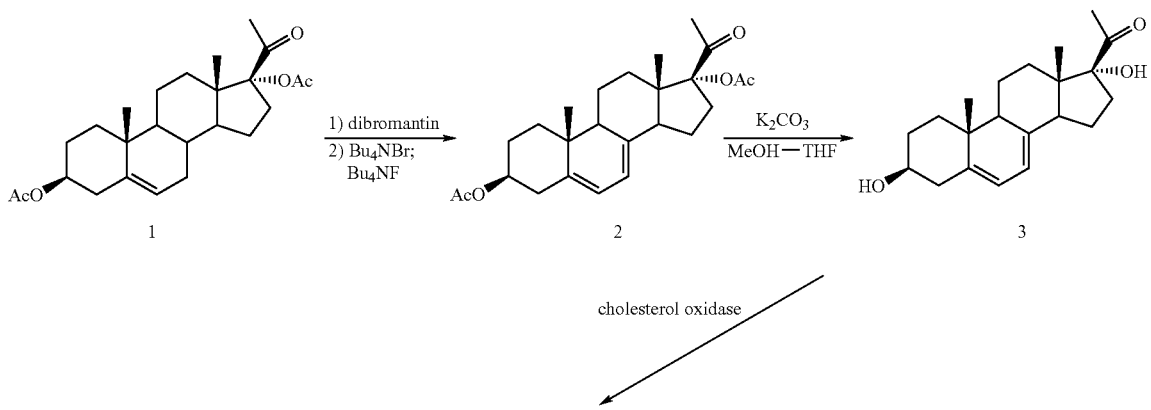

-continued

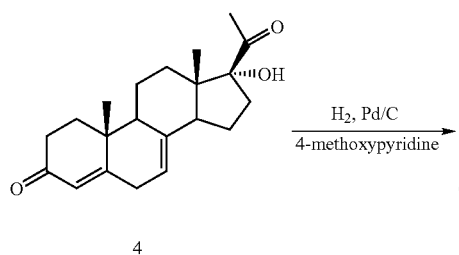

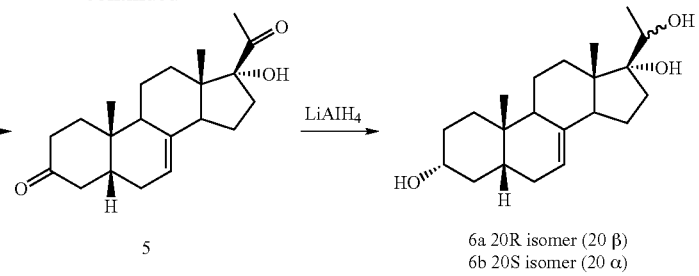

4

5

6a 20R isomer (20 β)
6b 20S isomer (20 α)

The compound 5β-pregn-7-ene-3α,17α,20R-triol (6a) may be prepared from 17α-hydroxypregneneolone diacetate (1), which is commercially available, by a variety of synthetic routes using synthetic chemical techniques well known to those skilled in the art. In one synthetic approach, shown in Scheme 5 and described more fully in the following examples, 5β-pregn-7-ene-3α,17α,20R-triol was prepared by first forming pregna-5,7-diene-3β,17α-diol-20-one diacetate (2), the 7-dehydro derivative of the hydroxypregneneolone diacetate (1). The diacetate (2) was then hydrolyzed to form the diol 3β,17α-dihydroxypregna-5,7-dien-20-one (3), which was treated with cholesterol oxidase to form the dione 17α-hydroxypregna-4,7-diene-3,20-dione (4). The dione (4) in turn was selectively hydrogenated to remove the 4,5 unsaturation and yield the dione 17α-Hydroxy-5β-pregn-7-ene-3,20-dione (5). The dione (5) was reduced to provide the triols 5β-pregn-7-ene-3α,17α,20R-triol (6a) and 5β-pregn-7-ene-3α,17α,20S-triol (6b).

An exemplary scheme for synthesis of 7-DHPT is described in the Examples below.

Use of the Isolated SLOS Analytes and Derivatives Thereof

SLOS diagnosis can involve detection of 8-DHE$_3$ or 7-DHPT, or both. Thus, the compounds of the invention, and derivatives thereof, are useful as standards for such assays. Subjects who are of interest for diagnosis according to the methods of the present invention include any subject, including fetuses, which may be suspected of being affected by SLOS. Of particular interest is the screening of pregnant women who are suspected of having an SLOS-affected fetus, particular pregnant women have previously had an SLOS-affected child or carried an SLOS-affected fetus, and thus are "at risk" of having another SLOS-affected child or carrying another SLOS-affected fetus. Other subjects of interest for diagnosis include individuals, such as children and adults, in whom a diagnosis of SLOS is suspected.

Biological samples for analysis according to the method of the invention include any samples suspected of containing the SLOS analyte. The biological sample can be obtained from an adult, a child, in order to facilitate a diagnosis of SLOS. In the context of prenatal diagnosis, the sample is preferably maternal, i.e., does not require access to fetal tissues or amniotic fluid. Samples obtained by non-invasive means are of particular interest. Exemplary samples include, but are not necessarily limited to urine, blood, serum, plasma, and other blood-derived samples from a patient.

Detection of the SLOS analyte can be accomplished by any suitable means, including, but not necessarily limited to, gas chromatography (GC), gas chromatography followed by mass spectroscopy (GC/MS), high pressure liquid chromatograph (HPLC) or HPLC followed by MS (HPLC/MS). Exemplary methods for determining the amount of the SLOS analyte in a sample may take the form of subjecting the compound being subjected to MS after being eluted from any GC, HPLC or capillary electrophoresis (CE) column useful in the separation of steroids or derivatized steroids from a biological sample, and quantitating the intensity of characteristic mass spectroscopy ion peak(s) for that compound.

Chemically synthesized 7-DHPT and/or 8-DHE$_3$ compounds find particular use in calibrating the instrumentation used for the diagnostic assay to ensure accurate detection of these SLOS analytes in patient samples. While other steroids may be used for calibration for analysis instrumentation such as gas chromatography/mass spectrometry (GC/MS), those skilled in the art of GC/MS analysis would confer that the best calibration standard is a purified and synthesized sample of the compound to be analyzed. Thus, the diagnostic method of the invention may comprise both calibrating the analysis instrument with a chemically synthesized SLOS analyte and then completing the analysis by determining the ratios of the SLOS analyte/normal steroid counterpart as stated above. In another embodiments, the samples are prepared and/or derivatized for analysis by HPLC/MS instrumentation instead of GC/MS.

The ordinarily skilled artisan upon reading the present specification can readily design kits for use in diagnosis of SLOS. Such SLOS diagnostic kits can comprise, for example, at least one standard compound which is a SLOS analyte, where the SLOS analyte is 8-DHE$_3$ or 7-DHPT, which compound can be provided in a container such as a vial, particularly a sterile vial, and which is free of contaminants that may interfere with analytical techniques with which the compounds are to be used (e.g., GC, MS, GC/MS, and the like). Of particular interest is a container, such as a vial or other container, compatible for use with an analytical device, such as a chromatograph, mass spectrometer, and the like. The "standard compound" is used to calibrate the instrumentation used in the diagnostic assay, such as the calibration of GC and/or GC/MS instrumentation prior to running the assay. The "standard compound" can be used to produce a calibration curve of the SLOS analyte for quantitating the levels of SLOS analyte found in a sample.

The "standard compound" in some embodiments is not the SLOS analyte compound but is a derivatized SLOS analyte compound which is appropriate for the instrumentation utilized in the SLOS diagnostic assay. An exemplary "standard compound" for GC/MS analysis includes derivatives of 8-DHE3 or a derivative of 7-DHPT that is suitable for GC and/or GC/MS analysis (e.g., 8-DHE$_3$ and/or 7DHPT derivative produced by silyation, alkylation, acylation, and the like). The tris-trimethyl silyl (TMS) ether derivative of 8-DHE$_3$ is an example of such a derivative suitable for use GC and GC/MS analysis.

Derivatives of 8-DHE$_3$ and of 7-DHPT can be produced using methods well known in the art. Exemplary silyating reagents include HMDS (Hexamethyldisilzane), TMCS (Trimethylchlorosilane) TMSI (Trimethylsilylimidazole), BSA (Bistrimethylsilylacetamide), BSTFA (Bistrimethylsilyltrifluoroacetamide), MSTFA (N-methyl-trimethylsilyltrifluoroacetamide), TMS-DEA (Trimethylsilyldiethylamine), MTBSTFA (N-methyl-N-t-butyldimethylsilyltrifluoroacetamide), and Halo-methylsilyl derivatization reagents. (BMDMCS, and CMDMCS). Selection of suitable silyation reagents for modification of 8-DHE$_3$ and 7-DHPT is within the skil of the ordinary artisan. Exemplary acylating reagents include fluorinated anhydrides such as Trifluoroacetoic Anhydrides (e.g., Pentafluoropropionic Anhydride (PFPA), and Heptafluorobutyric Anhydride), Fluoracylimidazoles (e.g., Trifluoroacetylimidazole, Pentafluoropropanylimidazole, and Heptafluorobutyrylimidazole), N-Methyl-bis(trifluoroacetamide) (MBRFA), Pentafluorobenzoyl Chloride (PFBCI), and Pentafluoropropanol (PFPOH). For further discussion of derivatization of compounds of GC and/or GC/MS analysis see, e.g., Regis 2000 Chromatography Catalog; and Knapp, D. R. Handbook of Analytical Derivatization Reactions; John Wiley & Sons; New York, 1979.

Where desired the kit can contain both compounds, 7-DHPT and 8-DHE$_3$ or derivatives thereof. The compounds can be in the same or different containers, which containers are labeled accordingly (e.g., indicating the amount, purity, and the like of the compound contained therein). The kit can further contain instructions for analysis of the SLOS analyte in a biological sample from a subject. The kit may also comprise instructions for instrument calibration, sample preparation and protocols for completing the SLOS analysis and data interpretation. The kit can further comprise solutions for the preparation of biological samples for SLOS analysis.

When multiple samples are analyzed for SLOS analytes by GC/MS within a specific time period, such as 4 hours, 8 hours etc., calibration standards are analyzed to insure accurate results from the instrumentation. Prior to analyzing multiple patient samples, a standard mixture comprising PT, 7-DHPT(synthesized), estriol and 8-DHE$_3$ in known concentrations maybe ran to allow the GC/MS instrument to measure the steroids in this standard mixture to set response values based on the known concentrations of the steroids in the standard mixture. The standard mixture may also be ran at the end of the time period as well as during the time period for the multiple sample runs for a more reliable SLOS diagnosis. The standard mixture enables the multiple patient samples to be analyzed using the stored standard values for PT, 7-DHPT, E and 8-DHE$_3$ as a calibrant, and reports quantitative values per volume of biological sample analyzed. A data system maybe configured to determined the ratio of abnormal SLOS metabolites (7-DHPT and 8-DHE$_3$) to normal components (PT and E$_3$, respectively) which is the information needed to determine whether a patient is affected with SLOS or carrying a SLOS affected fetus.

EXAMPLES

The following examples are put forth so as to provide those of ordinary skill in the art with a complete disclosure and description of how to make and use the present invention, and are not intended to limit the scope of what the inventors regard as their invention nor are they intended to represent that the experiments below are all or the only experiments performed. Efforts have been made to ensure accuracy with respect to numbers used (e.g. amounts, temperature, etc.) but some experimental errors and deviations should be accounted for. Unless indicated otherwise, parts are parts by weight, molecular weight is weight average molecular weight, temperature is in degrees Centigrade, and pressure is at or near atmospheric.

Example 1

Identification and Chemical Synthesis of 8-DHE$_3$

Further validation of the non-invasive SLOS diagnostic methods of the invention involved the characterization, identification and production of authentic standards of estrogen metabolites unsaturated in ring B, structures (3) and (4), 7-DHE$_3$ and 8-DHE$_3$, respectively. It should be noted that these dehydroestriols are also of interest as candidate metabolites of equine steroids contained in Premarin®, which is widely used in estrogen replacement therapy ((a) Bhavnani, B. R. *Proc. Soc. Exp. Biol. Med.* 1998, 217, 6–16. (b) Bhavnani, B. R.; Cecutti, A. *J. Soc. Gynecol. Investig.* 1995, 2, 424 (Abstract No. 415).

In general, the synthesis of 8-DHE$_3$ was completed by converting Equilin (8) in three steps to 7-dehydroestriol, which was isomerized to 8-dehydroestriol as depicted in Scheme 3. The bromination of equilin with CuBr$_2$ in MeOH gave complex mixtures. 1D and 2D NMR analysis of standards and crude reaction mixtures led to identification of ten bromosteroids, which, together with equilenin and equilin, accounted for >95% of the steroids observed in most reactions. Knowledge of reporter signals for the numerous bromosteroids facilitated byproduct identification and optimization of reaction conditions. Thus, use of 3 equiv. of CuBr$_2$ in methanol led mainly to bromination in ring A, dehydrogenation to equilenins, and rapid conversion of the desired 16-bromosteroids 9a and 9b to dibromides and equilenins (Table 2, entries 1–2). Shorter reaction times and a smaller excess of CuBr$_2$ resulted in large amounts of unbrominated steroids (8 and 10) and low conversion to the desired products (Table 2, entries 3–5).

In THF, the yield of 16-bromoequilins doubled to 21%, but the product still consisted mainly of equilenins and ring A brominated equilins (Table 2, entry 6). However, reaction in CHCl3-EtOAc gave >70% conversion to 16-bromoequilins (Table 2, entry 7), and these conditions were sufficiently reproducible to afford gram quantities of the desired products as a 2:1 mixture of 16α- and 16β-bromo epimers.

Under specific reaction conditions, this mixture was cleanly hydrolyzed to 16α-hydroxyequilin (7) without formation of 16-keto byproducts. Equilin (101 mg) and freshly ground CuBr$_2$ (166 mg) were heated in CHCl$_3$-EtOAc (25 mL each) for 2 h under vigorous reflux (to remove HBr). The crude product (140 mg; 48% 9a, 24% 9b) was stirred for 1.5 h at rt in DMF-water (3:1, total 10 mL) containing 2 equiv NaOH. MPLC on silica gel (EtOAc-hexane 3:7) gave 7 (78 mg, containing some $\Delta^{6,8}$ material). Attempts to purify 7 by reverse-phase HPLC (MeOH—H$_2$O 35:65) gave a 19:1 mixture of 7 and its $\Delta^{6,8}$ analog. Consequently, the equilenins formed during bromination and hydrolysis were removed after reduction of 7 to 3. NMR (CDCl$_3$, 25° C.): 9a δ 0.814 (s), 4.589 (d, 7.3 Hz), 5.449 (m); 9b δ 0.995 (s), 4.263 (t, 8 Hz), 5.500 (m); 7 δ 0.865 (s), 4.420 (d, 8.3 Hz), 5.509 (m). Reduction of 7 with NaBH$_4$ led to the target 7-dehydroestriol (3). Ketol 7 (446 mg) was reduced with NaBH$_4$ (47 mg) in MeOH (25 mL) for 2 h at 0° C. Methanol was removed at <20° C. in a stream of N$_2$ (higher temperatures resulted in formation of 15). Addition of cold saturated NH$_4$Cl (10 ml) followed by extraction with EtOAc gave 3 (452 mg, 81% purity). HPLC purification (250×21.2 mm C$_{18}$ column, MeOH—H$_2$O 45:55) of a 50-mg sample gave 3 (35 mg, 99% purity).

TABLE 2

Bromination of equilin (8) with CuBr$_2$: effects of reaction conditions on product distribution[a]

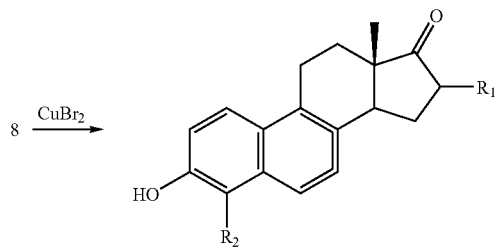

| | Δ$^7$ | | Δ$^{6,8}$ | |
|---|---|---|---|---|
| 8 | R$_1$ = H | R$_2$ = H | 10 R$_1$ = H | R$_2$ = H |
| 9a | R$_1$ = αBr | R$_2$ = H | 11a R$_1$ = αBr | R$_2$ = H |
| 9b | R$_1$ = βBr | R$_2$ = H | 11b R$_1$ = βBr | R$_2$ = H |
| 9c | R$_1$ = αBr | R$_2$ = Br | 11c R$_1$ = αBr | R$_2$ = Br |
| 9d | R$_1$ = βBr | R$_2$ = Br | 11d R$_1$ = βBr | R$_2$ = Br |
| 9e | R$_1$ = H | R$_2$ = Br | 11e R$_1$ = H | R$_2$ = Br |

TABLE 2-continued

Bromination of equilin (8) with CuBr$_2$: effects of reaction conditions on product distribution[a]

| entry | 1 | 2 | 3 | 4 | 5 | 6 | 7 |
|---|---|---|---|---|---|---|---|
| solvent | | MeOH | | | | THF | C-EA[b] |
| CuBr$_2$[c] | 3.0 | 3.0 | 1.6 | 1.6 | 1.6 | 1.0 | 1.2 |
| t (min) | 30 | 90 | 5 | 15 | 30 | 80 | 90 |
| %9a | 10 | 0 | 6 | 9 | 10 | 16 | 48 |
| %9b | 2 | 0 | 2 | 2 | 1 | 5 | 24 |
| %9c | 9 | 4 | 8 | 5 | 4 | 3 | 0 |
| %9d | 11 | 24 | 1 | 2 | 2 | 1 | 2 |
| %9e | 2 | 4 | 0 | 0 | 0 | 0 | 1 |
| %11a | 0 | 0 | 2 | 4 | 5 | 1 | 7 |
| %11b | 0 | 0 | 0 | 0 | 1 | 1 | 3 |
| %11c | 35 | 32 | 19 | 18 | 15 | 16 | 1 |
| %11d | 21 | 30 | 1 | 2 | 2 | 5 | 4 |
| %11e | 5 | 6 | 0 | 1 | 0 | 2 | 2 |
| %8 | 7 | 0 | 34 | 20 | 15 | 42 | 6 |
| %10 | 0 | 0 | 17 | 22 | 28 | 1 | 1 |

[a]Product distributions were determined by $^1$H NMR. Desired products (9a and 9b) are highlighted.
[b]Chloroform-ethyl acetate 1:1.
[c]Molar ratio of CuBr$_2$ to 8.

With the intention of synthesizing 8-dehydroestriol (4) by a parallel bromination-hydrolysis-reduction scheme, we prepared 8-dehydroestrone (12) by isomerizing equilin with LiNHCH$_2$CH$_2$NH$_2$ in ethylenediamine (Scheme 6). However, refluxing 12 with CuBr$_2$ in CHCl$_3$-EtOAc resulted in virtually no bromination at C-16 or in ring A, the product consisting of a 1:1:2 mixture of 10, 12, and 9(11)-dehydroestrone.

Scheme 6.[a]

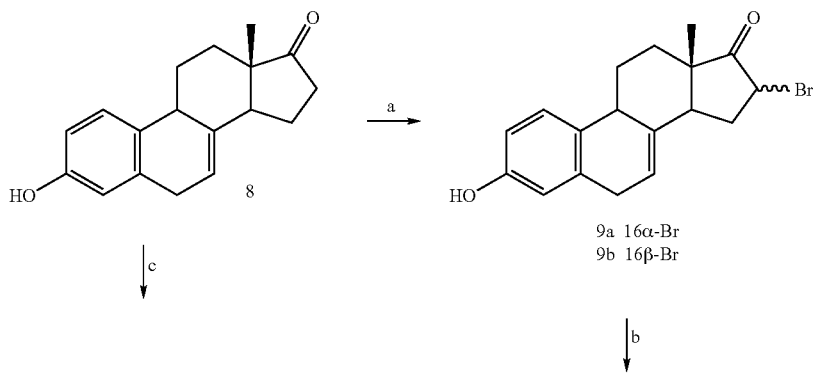

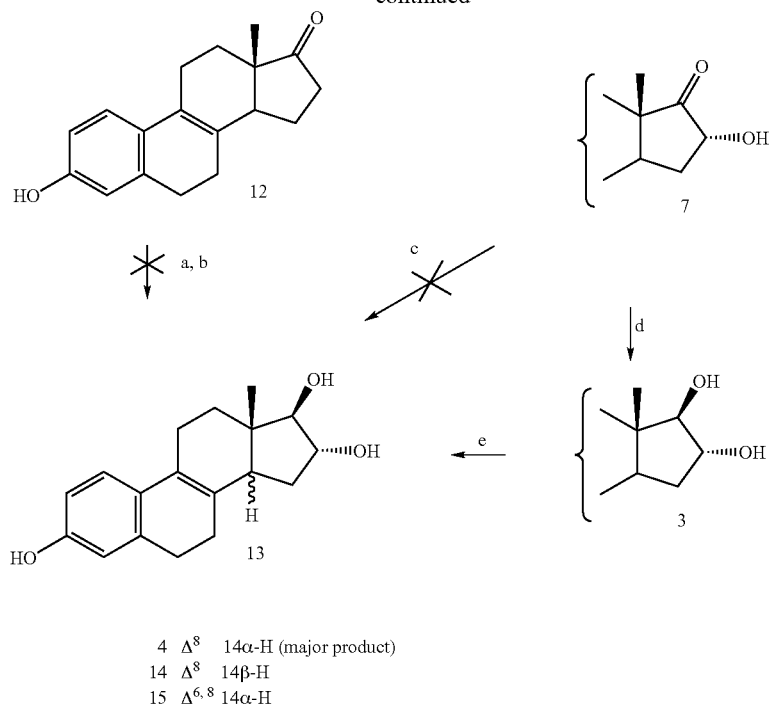

4  Δ⁸   14α-H (major product)
14 Δ⁸   14β-H
15 Δ⁶,⁸ 14α-H

An alternative attempt to prepare 13 by LiNHCH₂CH₂NH₂ isomerization of 7 gave none of the expected products. Reaction of 7 (50 mg) with 0.3 M Li in ethylenediamine (3 ml) gave mainly unreacted 7, whereas 1 M Li led to a complex mixture. However, isomerization of triol 3, which lacks the potentially labile 16,17-ketol functionality of 7, was more promising. Despite the poor solubility of 3 and its sluggish rate of isomerization, reaction conditions were found to give 4 as the major product. Dehydroestriol 3 (100 mg) was heated at 40° C. for 48 h in ethylenediamine (3.4 mL) containing LiNHCH₂CH₂NH₂ (prepared by adding 13.4 mmol of MeLi—LiBr in ether to ethylenediamine, followed by evaporation of the ether at 55° C.). NMR of the crude product (104 mg) indicated a 9:5:3:3 mixture of 4, 3, 14, and 15. Preparative HPLC (250×21.2 mm C₁₈ column, MeOH—H₂O 35:65, 7 mL/min) gave 14 ($t_R$ 146 min), 15 ($t_R$ 159 min), 3 ($t_R$ 165 min), and 4 ($t_R$ 172 min). NMR (CD₃OD, 25° C.): 3 δ 0.636 (s), 3.578 (d, 5.4 Hz), 4.043 (ddd, 9.1, 5.4, 2.0 Hz), 5.358 (br d, 3.4 Hz); 4 δ 0.757 (s), 3.549 (d, 5.3 Hz), 4.119 (ddd, 9.0, 5.3, 1.8 Hz); 14 δ 0.946 (s), 3.560 (d, 6.9 Hz), 3.999 (ddd, 8.8, 7.9, 6.9 Hz); 15 δ 0.667 (s), 3.668 (d, 5.6 Hz), 4.228 (ddd, 9.1, 5.6, 2.1 Hz). The forcing isomerization conditions resulted in partial epimerization of 4 to 14 and prompted a thorough structure of determination of all products by NMR. In contrast, byproducts were negligible in the preparation of 12 (3% 3, 1% 6-dehydroestrone, and 1–2% 14β steroids) and are frequently absent in base-catalyzed olefin isomerizations. Semipreparative reverse-phase HPLC afforded 4, 14, and 15, which were characterized by 2D NMR and NOE difference spectroscopy to confirm the regio- and stereochemical structure assignments.

With availability of authentic samples of the dehydroestriols, we compared their GC mobilities and mass spectral fragmentation with those of the SLOS urinary metabolites (FIG. 1). FIG. 1 is the GC/MS spectra of tris-TMS derivatives of authentic 7-dehydroestriol (A), 8-dehydroestriol (B), and the dehydroestriol isolated from urine (C). The molecular ions are at m/z 502, and major fragments are formed by losses of trimethylsilanol (−90) and methyl groups (−15). GC retention times for A, B and C were 18.77±0.03 min.

Isolation of dehydroestriols: Urine from a pregnant woman carrying an SLOS fetus was processed by standard methods for analyzing urinary steroids: (Shackleton, C. H. L. *J. Steroid Biochem. Mol. Biol.* 1993, 45, 127–140). Briefly, steroid sulfates and glucuronides from a C₁₈ solid phase extraction (SPE) of the urine sample were hydrolysed with *Helix pomatia* (Roman snail) digestive juice (Sigma-Aldrich). The resulting unconjugated steroids were reextracted by SPE and fractionated on Sephadex LH-20 (100× 10 mm column; cyclohexane-ethanol 4:1) as described: Setchell, K. D.; Shackleton, C. H. L. *Clin. Chim. Acta* 1973, 47, 381–388. GC/MS analysis of individual 5-mL fractions (as TMS ethers) revealed that dehydroestriol was eluted between 140 and 165 mL. The only two steroids found in this fraction were dehydroestriol and didehydroestriol 15. Although the TMS ethers of 7- and 8-dehydroestriols coeluted on the non-polar column used and shared the same parent and fragment ions, the isomers could be distinguished by the relative abundance of these ions. The steroid isolated from urine had the abundance profile of 8-dehydroestriol. This finding does not completely exclude production and excretion of 7-dehydroestriol by SLOS patients since only a few affected individuals have so far been studied. In addition, 7-dehydroestriol is less stable and may undergo aromatization to the didehydroestriol (15) found in urine.

In conclusion, we have developed simple and efficient methods for preparing estrogen metabolites unsaturated in ring B. The availability of these reference dehydroestriols will facilitate the establishment of routine noninvasive prenatal diagnosis for SLOS utilizing 8-DHE₃.

Example 2

Chemical Synthesis of 5β-Pregn-7-ene-3α,17α,20R-triol

5β-Pregn-7-ene-3α,17α,20R-triol and its 20S isomer (6a and 6b) were prepared in five steps from the commercially available 17α-hydroxypregnenolone diacetate (1). The chemical synthesis is shown in Scheme 5. A detailed description of one embodiment of the chemical synthesis of 7-DHPT is described below.

Source of reagents. Reagents, including dibromantin, tetrabutylammonium bromide, tetrabutylammonium fluoride, cholesterol oxidase, catalase, and 4-methoxypyridine-N-oxide were obtained from Sigma-Aldrich (Milwaukee, Wis.). 4-Methoxypyridine was obtained by hydrogenation of 4-methoxypyridine-N-oxide over Raney nickel. Solvents were Omnisolve grade from EM Science (Gibbstown, N.J.).

Pregna-5,7-diene-3β,17α-diol-20-one diacetate (2). To a solution of 17α-hydroxypregnenolone diacetate (1; 2.03 g, 4.8 mmol) in benzene-hexane 1:1 (120 ml) was added dibromantin (0.84 g, 2.92 mmol, 1.2 equiv.) and AIBN (32 mg). The mixture was refluxed under nitrogen for 10 min in a preheated 100° C. oil bath and then placed in an ice bath to cool. The insoluble materials were removed by suction filtration. The reaction flask and the insoluble materials were washed with an additional 20 ml of benzene. The filtrate was concentrated to a yellow solid using a rotary evaporator at 35° C. To a solution of this yellow solid in anhydrous THF (40 ml) was added tetrabutylammonium bromide (0.4 g). The resulting solution was stirred for 75 min under nitrogen at room temperature.

To this reaction mixture was added tetrabutylammonium fluoride (10 ml, 1 M solution in THF, 10 mmol, 2.1 equiv.). The resulting dark brown solution was stirred for an additional 50 min, followed by evaporation to a brown solid using a rotary evaporation at 40–45° C. A solution of this solid in ethyl acetate (200 ml) was washed with three portions of water (50 ml each) and dried over anhydrous $Na_2SO_4$. The evaporation of solvent gave crude 2 (2.03 g), which was subjected to MPLC (230–410 mesh silica gel; 370×25 mm i.d. column; elution with hexane-ethyl acetate 95:5, 4000 ml and hexane-ethyl acetate 92:8, 2000 ml). Fraction volumes were 20 ml. Fractions 29–42 gave an unidentified byproduct (34 mg). Fractions 161–173 gave pure unreacted starting material (1; 60 mg). Fractions 184–198 gave a mixture of 2 and starting material. Fractions 199–257 gave 2 (0.97g, 49%) of ca. 95% purity (containing 0.5–2.5% each of several minor olefins). $^1H$ NMR ($CDCl_3$), δ 0.587 (s, 3H), 0.949 (s, 3H), 2.075 (s, 3H), 4.715 (m, 1H), 5.451 (m, 1H), 5.577 (m, 1H).

3β,17α-Dihydroxypregna-5,7-dien-20-one (3). To a solution of diacetate 2 (100 mg) in a 1:2 mixture of tetrahydrofuran and methanol (24 ml) was added potassium carbonate (140 mg). The resulting mixture was sparged with nitrogen and then stirred at room temperature under nitrogen for 46 h. After completion of the reaction as judged by TLC, water (60 ml) was added. The resulting mixture was extracted with ethyl acetate (2×60 ml). The combined organic phase was washed with water (2×30 ml) and dried over anhydrous $Na_2SO_4$. Evaporation of solvent gave a white solid (64 mg), which was dissolved in methanol and precipitated by addition of water to give a white solid (56 mg, 71% yield) of high purity.

17α-Hydroxypregna-4,7-diene-3,20-dione (4). A solution of 3 (25 mg, 0.075 mmol) in butyl acetate (7 ml) was added to a TES buffer solution (6 ml, 50 mM, pH 7.5) containing cholesterol oxidase from Streptomyces species (50 units, 2.6 mg, 19 units/mg solid) and catalase (31 uml, 25 mg/ml, 51100 units/mg, 40000 units). The two-phase mixture was stirred in a vial at room temperature with a magnetic stirrer for 17 h. Ethyl acetate (20 ml) was added to the reaction mixture, and the separated organic phase was washed with water and brine, and dried over $Na_2SO_4$. Evaporation of solvent gave crude 4 (24 mg) as a nearly colorless solid.

17α-Hydroxy-5β-pregn-7-ene-3,20-dione (5). To a solution of 4 (20 mg) in 4-methoxypyrdine (1.5 ml) was added palladium on carbon (20 mg, 10% palladium by weight). The resulting mixture was stirred at room temperature under a hydrogen-filled balloon for 16 h. The catalyst was filtered through a cotton-plugged pipette containing Celite. Removal of solvent by bulb-to-bulb distillation gave crude 5 (20 mg) as a nearly colorless solid.

5β-Pregn-7-ene-3α,17α,20R-triol (6a) and 5β-pregn-7-ene-3α,17α,20S-triol (6b). To a solution of 5 (20 mg) in ether (5 ml) was added $LiAlH_4$ (50 mg). The resulting mixture was refluxed in a 55 deg C. oil bath for 2 h, followed by addition of cold 5% HCl (5 ml) to quench the reaction. The organic phase was separated, washed with water, dried over anhydrous $Na_2SO_4$. Evaporation of solvent gave a crude product (21 mg) comprising a mixture of C-20 epimers 6a and 6b. A portion (10 mg) of this mixture was subjected to preparative reverse-phase HPLC using a Phenomenex Prodigy 5u ODS(3) column (250×21.2 mm, UV detection at 210 nm). Elution with 80% MeOH in water (9 ml/min) gave homogenous samples of the 20R isomer 6a (3.4 mg, $t_R$ 21.1 min) and the 20S isomer 6b (3.1 mg, $t_R$ 23.1 min).

While the present invention has been described with reference to the specific embodiments thereof, it should be understood by those skilled in the art that various changes may be made and equivalents may be substituted without departing from the true spirit and scope of the invention. In addition, many modifications may be made to adapt a particular situation, material, composition of matter, process, process step or steps, to the objective, spirit and scope of the present invention. All such modifications are intended to be within the scope of the claims appended hereto.

That which is claimed is:

1. A composition comprising isolated 8-dehydro-estriol (8-$DHE_3$), or a salt or derivative thereof.

2. A kit comprising the composition of claim 1 in a container.

3. The composition of claim 1, wherein the composition comprises a silyalted derivative of 8-$DHE_3$.

4. A method for synthesis of 8-dehydro-estriol (8-$DHE_3$), the method comprising:
   contacting equilin with a halogen to form a 16-haloequilin;
   hydrolyzing the 16-haloequilin to yield 16α-hydroxyequlilin;
   reducing 16α-hydroxyequlilin to yield 7-dehydroestriol; and
   treating 7-dehydroestriol with a lithium compound;
   wherein 8-$DHE_3$ is produced.

5. Isolated 8-$DHE_3$ made by the method of claim 4.

6. A composition comprising isolated 5β-pregn-7-ene-3α,17α,20α-triol (7-DHPT) or a salt or derivative thereof.

7. A kit comprising the composition of claim 6 in a container.

8. The composition of claim 6, wherein the composition comprises a silyalted derivative of 7-DHPT.

9. A method for synthesis of 5β-pregn-17-ene-3α,17α,20α-triol (7-DHPT), the method comprising:

hydrolyzing pregna-5,7-diene-3β,17α-diol-20-one diacetate to form diol 3β,17α-dihydroxypregna-5,7-dien-20-one;

treating diol 3β,17α-dihydroxypregna-5,7-dien-20-one with a cholesterol oxidase to form 17α-hydroxypregna-4,7-diene-3,20-dione;

hydrogenate 17α-hydroxypregna-4,7-diene-3,20-dione to yield 17α-hydroxy-5β-pregn-7-ene-3,20-dione; and reducing 17α-hydroxy-5β-pregn-7-ene-3,20-dione;

wherein 5β-pregn-7-ene-3α,17α,20α-triol is produced.

10. The composition of claim 1 comprising isolated 8-dehydro-estriol (8-DHE$_3$), or a salt thereof.

11. The composition of claim 6 comprising isolated 5β-pregn-7-ene-3α,17α,20α-triol (7-DHPT) or a salt thereof.

12. The kit of claim 2 further comprising one or more solutions for the preparation of biological samples for SLOS analysis.

13. The kit of claim 7 further comprising one or more solutions for the preparation of biological samples for SLOS analysis.

14. The kit of claim 2 further comprising instructions for instrument calibration, sample preparation, and protocols for completing SLOS analysis and data interpretation.

15. The kit of claim 7 further comprising instructions for instrument calibration, sample preparation, and protocols for completing SLOS analysis and data interpretation.

* * * * *

UNITED STATES PATENT AND TRADEMARK OFFICE
CERTIFICATE OF CORRECTION

| | | |
|---|---|---|
| PATENT NO. | : 7,105,637 B2 | Page 1 of 1 |
| APPLICATION NO. | : 10/367096 | |
| DATED | : September 12, 2006 | |
| INVENTOR(S) | : Cedric Shackleton et al. | |

It is certified that error appears in the above-identified patent and that said Letters Patent is hereby corrected as shown below:

In column 1 line 18: Delete "may have" and replace with "has".

Signed and Sealed this
First Day of March, 2011

David J. Kappos
*Director of the United States Patent and Trademark Office*